US011278193B2

United States Patent
Kim et al.

(10) Patent No.: US 11,278,193 B2
(45) Date of Patent: Mar. 22, 2022

(54) MICRO ENDOSCOPE CAMERA MODULE AND MICRO ENDOSCOPE HAVING SAME

(71) Applicant: HAESUNG OPTICS, Hwaseong-si (KR)

(72) Inventors: Seong Hun Kim, Hwaseong-si (KR); Jae Son Yi, Hwaseong-si (KR)

(73) Assignee: HAESUNG OPTICS, Hwaseong-si (KR)

( * ) Notice: Subject to any disclaimer, the term of this patent is extended or adjusted under 35 U.S.C. 154(b) by 280 days.

(21) Appl. No.: 16/339,280

(22) PCT Filed: Nov. 2, 2017

(86) PCT No.: PCT/KR2017/012292
§ 371 (c)(1),
(2) Date: Apr. 3, 2019

(87) PCT Pub. No.: WO2018/105894
PCT Pub. Date: Jun. 14, 2018

(65) Prior Publication Data
US 2021/0093174 A1    Apr. 1, 2021

(30) Foreign Application Priority Data
Dec. 6, 2016    (KR) .................. 10-2016-0165064

(51) Int. Cl.
*A61B 1/05* (2006.01)
*A61B 1/06* (2006.01)
*A61B 1/07* (2006.01)

(52) U.S. Cl.
CPC ................ *A61B 1/051* (2013.01); *A61B 1/05* (2013.01); *A61B 1/0607* (2013.01); *A61B 1/07* (2013.01)

(58) Field of Classification Search
None
See application file for complete search history.

(56) References Cited

U.S. PATENT DOCUMENTS 4,491,865 A * 1/1985 Danna ..................... H04N 7/183
348/71
4,918,521 A * 4/1990 Yabe ................... A61B 1/00179
348/373

(Continued)

FOREIGN PATENT DOCUMENTS

JP      H08150113 A    6/1996
JP      2007014653 A   1/2007

(Continued)

OTHER PUBLICATIONS

International Search Report for Corresponding International Application No. PCT/KR2017/012292 (2 Pages) (dated Jan. 19, 2018).

*Primary Examiner* — John P Leubecker
(74) *Attorney, Agent, or Firm* — Lucas & Mercanti, LLP

(57) ABSTRACT

The present invention relates to a micro endoscope camera module, including a first tube body having one or more objective lenses disposed therein; and a second tube body supporting the first tube body at a one side, wherein an image capturing means is disposed to be adjacent to a rear portion of the objective lens inside the second tube body. In addition, the present invention relates to a micro endoscope, in which the above-described micro endoscope camera module is disposed at the tip end of the scope, whereby it is possible to realize a high-quality image acquisition by disposing the image capturing means for image acquisition at the front end of the scope.

7 Claims, 5 Drawing Sheets

(56) References Cited

U.S. PATENT DOCUMENTS

| | | | |
|---|---|---|---|
| 6,547,722 B1* | 4/2003 | Higuma | A61B 1/00096 600/133 |
| 2006/0183977 A1* | 8/2006 | Ishigami | A61B 1/0684 600/179 |
| 2007/0112247 A1* | 5/2007 | Hirata | A61B 1/0684 600/101 |
| 2013/0137925 A1* | 5/2013 | Ushijima | A61B 1/0008 600/109 |
| 2015/0240137 A1* | 8/2015 | Yokoyama | G02B 23/2476 600/133 |
| 2017/0064162 A1* | 3/2017 | Haraguchi | A61B 1/00096 |
| 2019/0004308 A1* | 1/2019 | Iwama | G02B 23/2484 |

FOREIGN PATENT DOCUMENTS

| | | | |
|---|---|---|---|
| JP | 2015047277 A | | 3/2015 |
| JP | 2015047278 A | * | 3/2015 |
| JP | 2015047278 A | | 3/2015 |
| KR | 10-2015-0010281 A | | 1/2015 |

\* cited by examiner

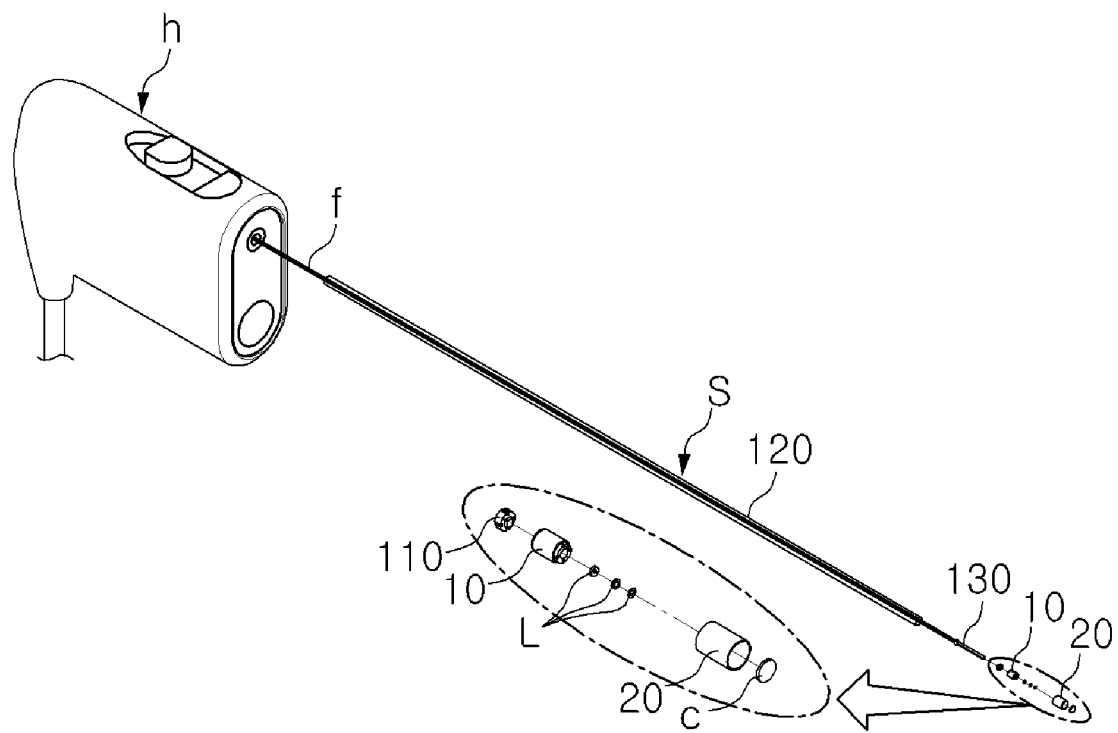
[FIG. 1]

[FIG. 2]
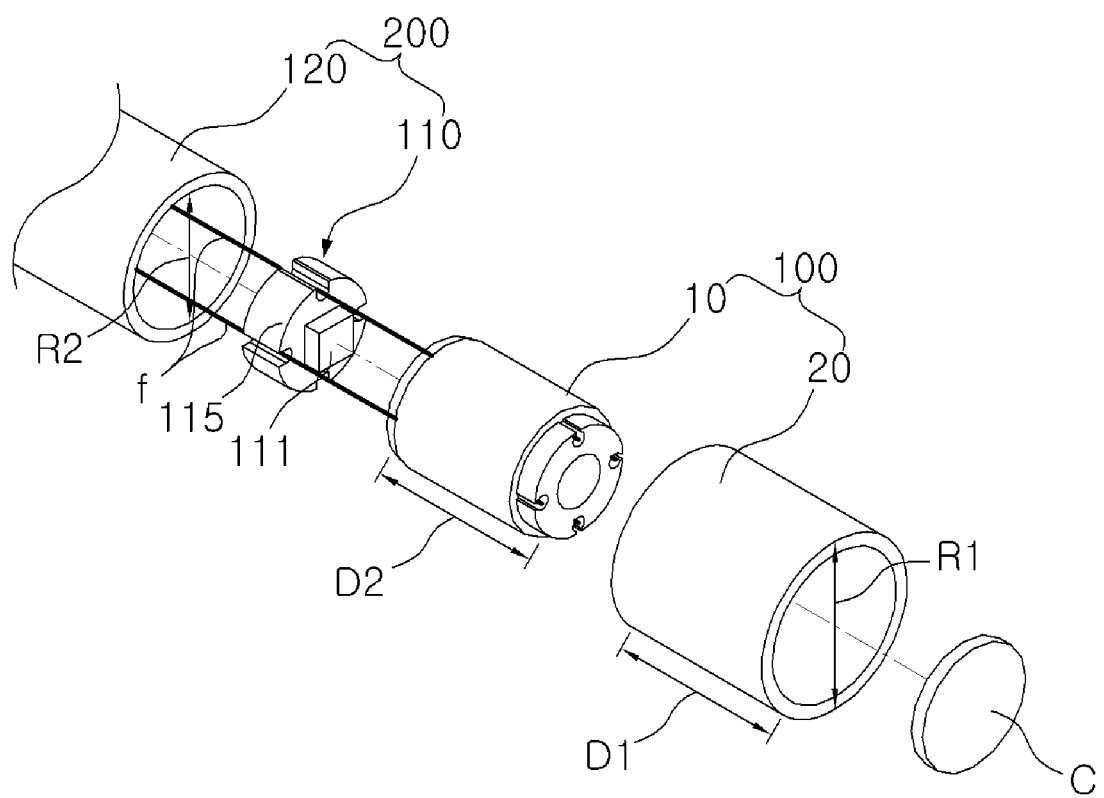

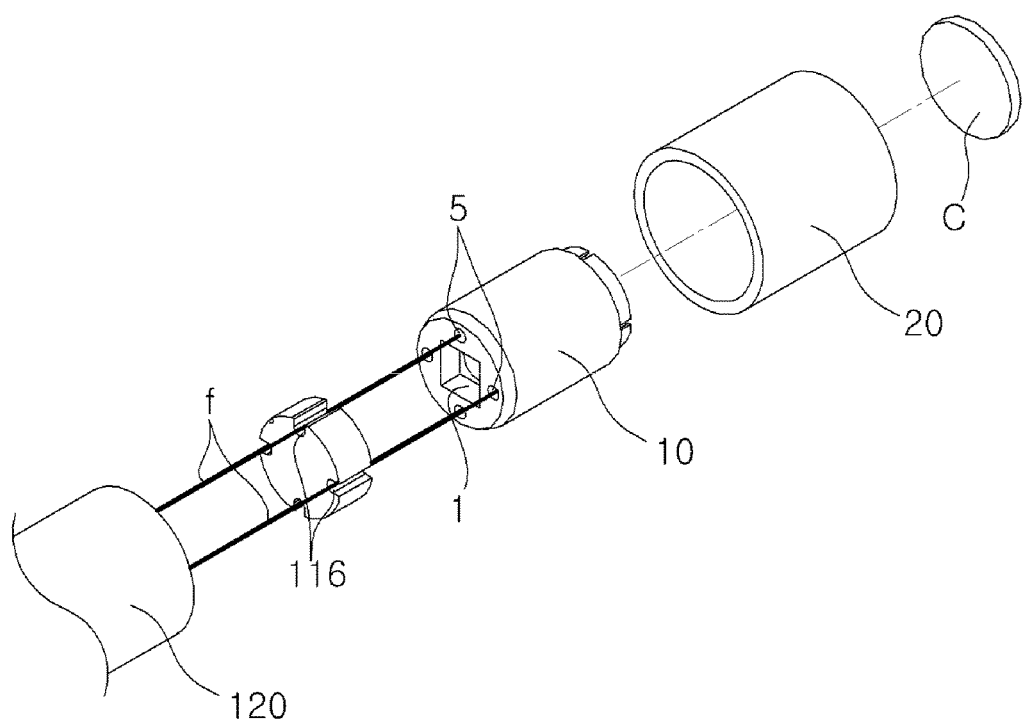
[FIG. 3]

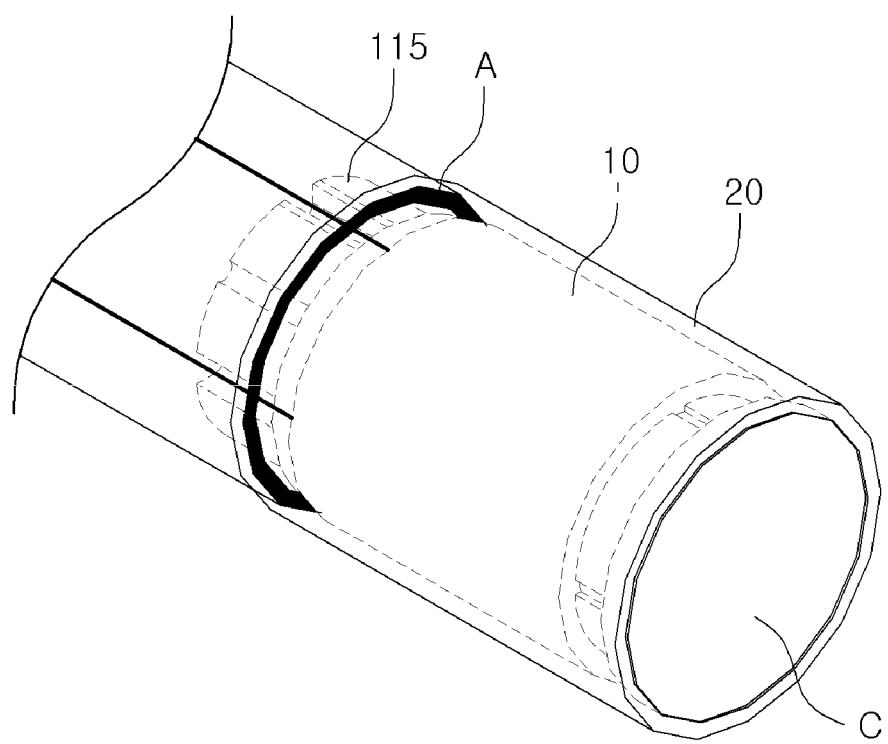
[FIG. 4]

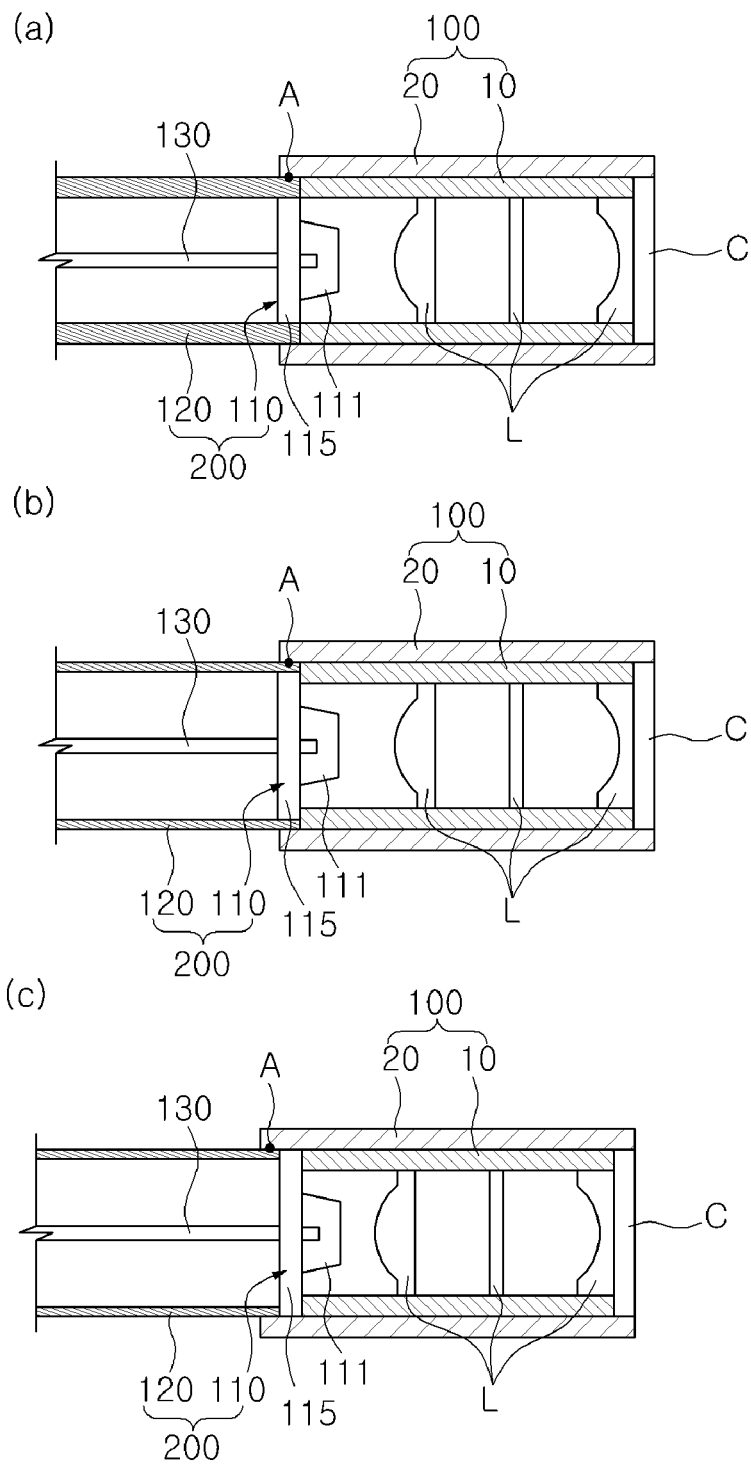
[FIG. 5]

MICRO ENDOSCOPE CAMERA MODULE AND MICRO ENDOSCOPE HAVING SAME

Cross-Reference to Related Applications

This application is a 371 U.S. national stage of PCT/KR2017/012292, filed Nov. 2, 2017 which claims the priority from Korean Patent Application No. 10-2016-0165064, filed Dec. 6, 2016, the contents of each of which are incorporated herein by reference.

TECHNICAL FIELD

The present invention relates to a micro endoscope camera module and a micro endoscope having the same.

BACKGROUND ART

An endoscope is a kind of optical instrument and largely classified into an industrial endoscope for inspecting small enclosed spaces such as pipes and ships, and a medical endoscope for inspecting the inside the human body.

Among endoscopes, the medical endoscope is an apparatus for visually checking and diagnosing the inside of the human body by directly inserting the endoscope into the human body and imaging the inside. Medical endoscopes are classified into a fiberoptic endoscope and an electronic endoscope.

Here, the fiberoptic endoscope is provided in such a manner as to acquire an image by incorporating an image transmitting means such as a relay rod lens or an optical fiber in a scope inserted into the human body and disposing an image sensor on a handle that is a grip portion. In the case of such an endoscope, there is a problem that the acquisition of a high-quality image is limited due to distortion and noise in the signal transmission process.

In the meanwhile, Korean Patent Application Publication Nos. 10-2014-0065231 and 10-2012-0101450, which are related to an electronic endoscope, are configured such that an objective lens, an image sensor, and a light source are all provided at an inner end of a scope that is inserted into the human body, so that a diameter of a tip end portion of the endoscope becomes large, whereby there is a problem that a severe rejection feeling occurs thus causing pain to a test subject when the endoscope is inserted into the human body.

DISCLOSURE

Technical Problem

Accordingly, the present invention has been made keeping in mind the above problems occurring in the prior art, and an object of the present invention is to provide an micro endoscope camera module and a micro endoscope having the same in which an image capturing means for image acquisition is disposed at the front end of a scope, thereby realizing high-quality image acquisition.

It is a further object of the present invention to provide a micro endoscope camera module and a micro endoscope having the same in which a scope is configured such that a scope tube having an objective lens accommodated therein is physically supported at the rear, thereby preventing the scope tube accommodated in the scope from being pushed backward during assembly or use.

It is still another object of the present invention to provide a micro endoscope camera module and a micro endoscope having the same in which an illumination fiber is configured to be guided into the scope tube and the image capturing means to allow light source to be provided through the illumination fiber, thereby reducing a diameter of the scope.

Technical Solution

In order to accomplish the above object, the present invention provides a micro endoscope camera module, including: a first tube body having at least one objective lens disposed therein; and a second tube body supporting the first tube body at a one side, wherein the second tube body is provided therein with an image capturing means disposed to be adjacent to a rear portion of the objective lens.

Here, the first tube body may include a scope tube having a receiving space in which the objective lens is held and supported and a front tube covering the outside of the scope tube.

Further, the second tube body may include the image capturing means and a main tube covering the outside of the image capturing means.

Here, an outer diameter of the front tube may be formed to be larger than an outer diameter of the main tube so that a rear end of the front tube is provided in such a manner as to surround a front end of the main tube.

Here, the first tube body may be disposed at a front end of a scope inserted into a human body.

Meanwhile, in order to accomplish the above object, the present invention provides a micro endoscope camera module, including: a scope tube having a receiving space in which at least one objective lens are held and supported; a front tube covering the outside of the scope tube; an image capturing means disposed at a rear end of the scope tube; and a main tube covering the outside of the image capturing means, wherein an outer diameter of the front tube is formed to be larger than an outer diameter of the main tube.

Here, the rear end of the scope tube may be in contact with a front end of the main tube in whole or in part.

Further, a length of the front tube may be formed to be larger than a length of the scope tube on the basis of a cross section.

Here, an overlap region may be provided in which a rear end of the front tube surrounds a front end of the main tube so that the front tube is coupled to the main tube at the overlap region via laser welding.

Here, the image capturing means may be provided with an image sensor onto which an image acquired through the objective lens is focused and a substrate electrically connected to the image sensor to allow the image sensor to be mounted thereon.

Further, the image sensor may be provided as any one of a CCD sensor or a CMOS sensor.

Meanwhile, the scope tube may include one or more illumination holes passing therethrough along a longitudinal direction.

Here, the illumination holes may be arranged circularly on a rear surface of the scope tube at regular angular intervals.

Further, a receiving recess in which the image sensor is received may be formed at a center of the rear surface of the scope tube.

Herein, a 'U'-shaped guide recess may be provided to allow an illumination fiber to be guided in correspondence with a position of the illumination hole at a circumference of the substrate.

Meanwhile, the object can be obtained by a micro endoscope having the micro endoscope camera module.

Advantageous Effects

According to the present invention, it is possible to realize high-quality image acquisition by disposing the image capturing means for image acquisition at the front end of the scope.

In addition, since the scope is configured such that a scope tube having an objective lens accommodated therein is physically supported at the rear, it is possible to prevent the scope tube accommodated in the scope from being pushed backward during assembly or use, thereby improving efficiency of the assembling process and securing usability.

In addition, an illumination fiber is provided to be guided into the scope tube and the image capturing means to allow a light source to be provided through the illumination fiber, thereby downsizing the scope diameter.

DESCRIPTION OF DRAWINGS

FIG. 1 is an exploded perspective view of an micro endoscope camera module and an micro endoscope having the same according to the present invention, FIG. 2 is a front exploded perspective view of an micro endoscope camera module according to the present invention, FIG. 3 is a rear exploded perspective view of a micro endoscope camera module according to the present invention, FIG. 4 is an assembled perspective view of a micro endoscope camera module according to the present invention, and FIGS. 5(a), 5(b), and 5(c) are sectional views showing embodiments of a micro endoscope camera module according to the present invention.

BEST MODE

Hereinafter, the configuration of the present invention will be described in detail with reference to the accompanying drawings.

Prior to the description, a detailed description of related art will be omitted if it is determined that the gist of the present invention may be unnecessarily obscured. Also, in this specification, when an element is referred to as being "connected" or "coupled" to another element, the element can be directly connected or directly coupled to the other element, but it is to be understood that the element may be connected or coupled via another component in between, unless explicitly mentioned to the contrary.

In other words, the terms used in the present specification and claims should not be construed in a dictionary meaning, but the inventor can define the concept of the term appropriately in order to explain the invention in the best way. Accordingly, the present invention should be construed as meaning and concept consistent with the technical idea of the present invention.

Therefore, the embodiments shown in the present specification and the drawings are only exemplary embodiments of the present invention, and not all of the technical ideas of the present invention are described. Therefore, at the time of the present application, it should be understood that various equivalents and modifications may be present without departing from the scope of the invention.

<Micro Endoscope>

FIG. 1 is an exploded perspective view of a micro endoscope camera module and a micro endoscope having the same according to the present invention.

Referring to FIG. 1, the micro endoscope according to the present invention includes a scope S coupled to a handle h. When the scope S is configured to be attachable to and detachable from the handle h, it is possible to realize an endoscope that does not require a cleaning and disinfection process by providing the scope S as a disposable product, or alternatively an endoscope in which the scope S and the handle h are integrated may be provided as a disposable product.

The handle h is made of a synthetic resin material or a metal material, and is provided to form a grip portion during endoscopic treatment and include a number of components for acquiring, processing, and transmitting an image.

Specifically, the handle h may include a plurality of operation buttons for photographing and capturing an image and a cable for signal transmission on the outer surface thereof.

In addition, the handle h includes an image signal processor (ISP) for processing the image that is focused onto the image sensor and transmitted through an optical fiber, an LED for providing a light source, a plurality of optical fibers (f, an optical fiber for image acquisition and an optical fiber for providing illumination) connected to the scope S for image transmission and light source transmission, a USB port for signal transmission to the outside, a holder and a printed circuit board for supporting and electrically connecting the above-described structures, and the like.

The scope S is configured to be inserted into the human body of the examinee to perform image acquisition and have a plurality of optical fibers disposed therein and a configuration for image acquisition disposed at the tip end (specifically described in the paragraph of a micro endoscopic camera module below).

The scope S may be made of various materials such as metal or synthetic resin, but it may be made of a hard material having a certain hardness or more.

The length of the scope S may be variously set according to the use of the endoscope, preferably 5 to 25 cm and more preferably 7 to 15 cm. In addition, the diameter of a tip end of the scope S is formed to be equal to or less than 3 mm, and it is possible to minimize a pain incidence and a rejection feeling of the examinee when being inserted into the human body.

<Micro Endoscope Camera Module>

FIG. 1 is an exploded perspective view of an micro endoscope camera module and an micro endoscope having the same according to the present invention, FIG. 2 is a front exploded perspective view of an micro endoscope camera module according to the present invention, FIG. 3 is a rear exploded perspective view of a micro endoscope camera module according to the present invention, FIG. 4 is an assembled perspective view of a micro endoscope camera module according to the present invention, and FIGS. 5(a), 5(b), and 5(c) are sectional views showing embodiments of a micro endoscope camera module according to the present invention.

Referring to FIGS. 1 to 5, the micro endoscope camera module according to the present invention includes a first tube body 100 in which one or more objective lenses L are disposed and a second tube body 200 that supports the first tube body 100 at one side. The second tube body 200 is provided therein with an image capturing unit 110 disposed adjacent to the rear of the objective lens L.

In the present invention, the first and second tube bodies 100 and 200 have the lens L and the image capturing means 110 accommodated therein respectively, and the tube bodies 100 and 200 are configured to be coupled by allowing the second tube body 200 to support the first tube body 100, thereby increasing ease of assembly process and reliability of use.

—First Tube Body—

The first tube body 100 is configured to form a tip end of the micro endoscope camera module and include a scope tube 10 having a receiving space in which one or more objective lenses L is held and supported, a front tube 20 covering the outside of the scope tube 10, and a cover glass C coupled to the tip end of the front tube 20 of the scope tube 10.

The objective lens L may be provided with one or more glass lenses or plastic lenses, and each lens may be provided in a form of a spherical surface or an aspheric surface or a combination thereof. In FIG. 5, as objective lens L, there are shown a total of three lenses, including, but not limited to, plane-concave lenses, a plane lens, and a plane-convex lens from the above. The number and type (a structure of the lens, a focal length of the lens, the F number, Abbe number, a lens interval, a curvature, a refractive index, whether or not adopt IR filter lens) of objective lenses L may be variously set according to target viewing angle. Each objective lens L has an outer diameter of 2 mm or less, preferably 1.5 mm or less, and is accommodated in the scope tube 10.

The scope tube 10 may be formed of a cylindrical synthetic resin material and configured to provide a space for receiving and holding the objective lens L described above and a means (an engaging jaw, an engaging groove, or the like) for securing the objective lens L accommodated therein.

In addition, the scope tube 10 includes four illumination holes 5 passing therethrough along a longitudinal direction as shown in FIG. 3, in which the four illumination holes 5 are arranged circularly on a rear surface of the scope tube 10 at regular angular intervals. The illumination holes 5 are configured to guide the illumination fiber f that transmits a light source emitted from an LED installed on a handle. In the present invention, in order to provide a uniform light source using four illumination fibers, a total of four illumination holes 5 are provided at regular intervals because four illumination fibers are used, but it is not limited thereto, and a plurality of illumination fibers and illumination holes may be set according to the required light amount.

Meanwhile, as shown in FIG. 3, the scope tube 10 is provided on a center of the rear surface thereof with a receiving recess 1 of a hexahedron shape for receiving an image sensor 111 to be described later. The image sensor 111 may be disposed in the receiving recess 1 and thus disposed adjacent to the rear side of the objective lens L, thereby acquiring a high quality image as compared with an objective system using a relay rod lens.

The front tube 20 is configured to cover the outside of the scope tube 10, and is coupled to a cover glass C at the front thereof, and has the scope tube 10 positioned inside. The outer diameter of the front tube 20 is 3 mm or less, preferably 2.5 mm or less.

Here, a length D1 of the front tube 20 is formed to be larger than a length D2 of the scope tube 10 on the basis of a cross section, because a clearance is defined at the rear end of the front tube 20 and thus the scope tube 10 is physically supported at the corresponding clearance through the main tube 120 or the substrate 115 so as to prevent the scope tube 10 from being pushed backward, which will be described later.

—Second Tube Body—

The second tube body 200 is configured to support the first tube body 100 in such a manner as to be in contact with the first tube body 100 and to include an image capturing means 110 disposed at the rear end of the scope tube 10 and the main tube 120 covering the outside of the image capturing means 110.

The image capturing means 110 is configured to acquire an image transmitted from the objective lens L and to include an image sensor 111 onto which an image is focused, a substrate 115 of cylindrical shape that is electrically connected to the image sensor 111 to allow the image sensor 111 to be mounted thereon, and a PCB 130 disposed in contact with a rear end of the substrate 115.

Here, the image sensor 111 may be any one of a CCD sensor or a CMOS sensor. The image sensor 111 is provided in a hexahedron shape and is mounted on the substrate 115, and is received in the receiving recess 1 of the scope tube 10 when manufacturing the scope S by coupling the first tube body 100 to the second tube body 200.

Here, as shown in FIGS. 2 and 3, around the substrate 115, 'U'-shaped guide grooves are provided to allow the illumination fibers f to be guided in correspondence with the positions of the illumination holes 5 of the scope tube 10. Specifically, the illumination fibers f connected through the scope S are guided through the guide grooves 116 of the substrate 115 and the illumination holes 5 of the scope tube 10 and thus arranged in front of the scope tube 10, whereby each of the illumination fibers f is reliably placed at the target position without twisting. Here, an optical fiber connected from the handle h is provided by allowing an optical fiber (not shown) for image transmission and the illumination fiber f to be bundled, in which the optical fiber for image transmission is electrically connected to the substrate 115 or the PCB 130 and the illumination fibers f are individually disposed in front of the scope tube 10 through the respective guide grooves 116 and the respective illumination holes 5 to provide illumination through the cover glass C.

The main tube 120 is configured to cover the outside of the image capturing means 110 and have the image capturing means 110 disposed at the front end and the optical fiber drawn out through the handle f disposed therein.

The front end of the main tube 120 is in contact with the rear end of the front tube 20 to be coupled to each other. An outer diameter R1 of the front tube 20 is larger than an outer diameter R2 of the main tube 120, whereby the front tube 20 and the main tube 120 are coupled in a state that the front tube 20 partially surrounds the main tube 120. A detailed description thereof will be described later.

—Arrangement and Coupling Relationship of the First Tube Body and the Second Tube Body—

The scope S is configured such that the first tube body 100 and the second tube body 200 are arranged in this order from the front side, whereby the first tube body 100 is disposed at the front end of the scope S.

Here, as shown in FIGS. 2 to 5, a diameter of the first tube body 100 is formed to be larger than a diameter of the second tube body 200 so that the rear end of the first tube body 100 partially surrounds the front end of the second tube body 200. Specifically, as shown FIGS. 2, 4, and 5, an outer diameter R1 of the front tube 20 is larger than an outer diameter R2 of the main tube 120 so that the rear end of the front tube 20 surrounds the front end of the main tube 120.

As described above, the length D1 of the front tube 20 is larger than the length D2 of the scope tube 10, according to the length relationship between the front tube 20 and the scope tube 10 and the outer diameter relation between the front tube 20 and the main tube 120, a clearance is formed at the rear end of the front tube 20 and the front end of the main tube 120 is inserted into the space, whereby the scope tube 10 is physically supported by the main tube 120 or the substrate 115. That is, the scope tube 10 is prevented from being pushed backward and being displaced.

Here, as shown in FIG. 5, the rear end of the scope tube 10 is supported in such a manner as to be in contact with the front end of the main tube 120 in whole or in part. The main tube 120 is connected to the rear end of the scope tube 10 in whole as shown in FIG. 5(*a*), or a part of the main tube 120 and a part of the substrate 115 are in contact with the rear end of the scope tube 10 as shown in FIG. 5(*b*), and the substrate 115 may totally contact the rear end of the scope tube 10 and the main tube 120 may be supported at the rear of the substrate 115 as shown in FIG. 5(*c*), thereby preventing the scope tube 10 from being pushed backward.

In addition, as shown in FIGS. 4 and 5, when arranging the above-described structure, an overlap region A is provided in which the rear end of the front tube 20 surrounds the front end of the main tube 120. The front tube 20 may be coupled to the main tube 120 in the overlap region A via laser welding (the optical axis adjustment and focusing adjustment process should be performed for the inner optical configurations before welding of each tube via welding).

As described above, the micro endoscope camera module and the micro endoscope having the same according to the present invention can realize high-quality image acquisition by disposing the imaging means for image acquisition at the front end of the scope.

In addition, since the scope is configured such that the scope tube having the objective lens accommodated therein is physically supported at the back, it is possible to prevent the scope tube accommodated in the scope from being pushed backward during assembly or use, thereby improving the efficiency of the assembling process and securing usability.

In addition, since the illumination fiber is provided to be guided into the scope tube and the image capturing means to allow a light source to be provided through the illumination fiber, a diameter of the scope can be reduced.

While the present invention has been described with reference to the exemplary embodiments and the drawings, it is to be understood that the technical scope of the present invention is not limited to these embodiments and various changes and modifications may be made by those skilled in the art. Various modifications and variations may be made without departing from the scope of the present invention.

INDUSTRIAL APPLICABILITY

The present invention can be widely used for various kinds of endoscopes.

The invention claimed is:

1. A micro endoscope camera module, comprising:
a scope tube having a receiving space in which an objective lens is held and supported;
a front tube covering the outside of the scope tube;
an image capturing means disposed at a rear end of the scope tube; and
a main tube covering the outside of the image capturing means, wherein an outer diameter of the front tube is formed to be larger than an outer diameter of the main tube,
wherein
the image capturing means is provided with an image sensor onto which an image acquired through the objective lens is focused and a substrate electrically connected to the image sensor to allow the image sensor to be mounted thereon;
the scope tube includes one or moe illumination holes passing therethrough along a longitudinal direction; and
a 'U'-shaped guide recess is provided to allow an illumination fiber to be guided in correspondence with a position of the illumination hole at a circumference of the substrate.

2. The micro endoscope camera module of claim 1, wherein the rear end of the scope tube is in contact with a front end of the main tube in whole or in part.

3. The micro endoscope camera module of claim 1, wherein a length of the front tube is formed to be larger than a length of the scope tube on the basis of a cross section.

4. The micro endoscope camera module of claim 3, wherein an overlap region is provided in which a rear end of the front tube surrounds a front end of the main tube so that the front tube is coupled to the main tube at the overlap region via laser welding.

5. The micro endoscope camera module of claim wherein the image sensor is selected from the group consisting of a CCD sensor and a CMOS sensor.

6. The micro endoscope camera module of claim 1, wherein the illumination holes are arranged circularly on a rear surface of the scope tube at regular angular intervals.

7. The micro endoscope camera module of claim 6, wherein a receiving recess in which the image sensor is received is formed at a center of the rear surface of the scope tube.

* * * * *